United States Patent [19]

Mielens

[11] 4,174,402

[45] Nov. 13, 1979

[54] METHOD FOR THE PROPHYLAXIS OF SRS-A-INDUCED SYMPTOMS

[75] Inventor: Zigurd E. Mielens, East Greenbush, N.Y.

[73] Assignee: Sterling Drug Inc., New York, N.Y.

[21] Appl. No.: 934,616

[22] Filed: Aug. 17, 1978

[51] Int. Cl.² .......................................... A61K 31/40
[52] U.S. Cl. .................................................. 424/274
[58] Field of Search ......................................... 424/274

[56] References Cited

U.S. PATENT DOCUMENTS

| 3,882,148 | 5/1975 | Augstein et al. | 260/345.2 |
| 3,948,939 | 4/1976 | Alexander et al. | 260/315 |

Primary Examiner—Leonard Schenkman

Attorney, Agent, or Firm—Frederik W. Stonner; B. Woodrow Wyatt

[57] ABSTRACT

A method for inhibiting the symptoms induced by SRS-A released in a mammal susceptible to said SRS-A which comprises administering to said mammal an amount effective for inhibiting said symptoms of a compound selected from the group consisting of 9-benzoyl-12,3,4,-tetrahydrocarbazole-3-carboxylic acid, 9-benzoyl-6-methoxy-1,2,3,4-tetrahydrocarbazole-3-carboxylic acid, 9-benzoyl-1,2,3,4-tetrahydrocarbazole-4-carboxylic acid, 9-(4-toluoyl)-1,2,3,4-tetrahydrocarbazole-4-carboxylic acid, 9-benzoyl-6-methoxy-1,2,3,4-tetrahydrocarbazole-4-carboxylic acid and 9-benzoyl-6-methyl-1,2,3,4-tetrahydrocarbazole-4-carboxylic acid; or a pharmaceutically acceptable salt of said compound.

12 Claims, No Drawings

METHOD FOR THE PROPHYLAXIS OF SRS-A-INDUCED SYMPTOMS

BACKGROUND OF THE INVENTION

1. Field of the Invention

This invention relates to a novel method for the prophylaxis and treatment of symptoms associated with certain allergic reactions, such as, allergic extrinsic asthma and allergic rhinitis.

2. Description of the Prior Art

Current drug treatment of allergic asthma includes β-adrenergic catecholamines, methylxanthines and, in severe cases, corticosteroids. However, such drugs have a broad spectrum of pharmacological activities, including effects other than anti-asthmatic effects, which limit their usefulness in asthma therapy. Thus there is a need for specific anti-asthmatic drugs. Such specific anti-asthmatic drugs would either antagonize the mediators of allergic bronchoconstriction e.g., histamine and SRS-A (slow reacting substance of anaphylaxis), or block the release of these mediators of allergic bronchoconstriction. An example of a specific anti-asthma drug that blocks the release of mediators of allergic reactions is disodium cromoglycate [Intal ®; The Merck Index, Ninth Edition (1976), 2585], which has been found to be useful mainly against allergic asthma.

In addition to drugs which block the release of mediators of anaphylaxis, a second type of specific anti-asthmatic drug would antagonize the mediators of allergic bronchoconstriction rather than block their release. Histamine is one well documented mediator of allergic bronchospasm in man, but antihistamines are notably ineffective against asthmatic attacks. This is believed to be attributable to the relatively small amount of histamine released as a result of reagenic antibody-antigen interaction compared to the amount of SRS-A released. SRS-A, which has a profound constrictor effect and long duration of action, is a well documented mediator of anaphylaxis in man [K. F. Austen, Fed. Proc. 33;2256–2262 (1974); H. M. Guirgis and R. G. Townley, J. Allergy 53:74 (1974); P. J. Piper and J. L. Walker, Br. J. Pharmac. 47:291–304 (1973)], monkeys and guinea pigs [D. J. Stechschulte, R. P. Orange and K. F. Austen, J. Immunol. 111:1585–1589 (1973); R. Liebig, B. Peskar and Bernauer, Arch. Pharmacol. 282 Suppl.: R-58 (1974)]; and calves [J. F. Burka and P. Eyre, Can. J. Physiol. Pharmacol. 52:1201–1204 (1974)]. U.S. Pat. 3,882,148 describes a class of compounds which are indicated to be antagonists of SRS-A and thus useful in the treatment of disorders in which SRS-A is a factor, for example asthma, hay fever and skin afflictions. Antagonism of SRS-A also has been reported for other compounds [J. Med. Chem. 20:371–379 (1977); Nature New Biol. 245:215–217 (1973)].

SUMMARY OF THE INVENTION

It has been discovered that certain compounds of the class of 9-benzoyl-1,2,3,4-tetrahydrocarbazole-3 (and 4)-carboxylic acids are antagonists of SRS-A as indicated in tests more fully described hereinbelow. Therefore these compounds are indicated for use in the prophylactic treatment of a mammal which is susceptible to symptoms induced by SRS-A. Symptoms where SRS-A has been shown to be a significant causative factor are, for example, allergic bronchial asthma and allergic rhinitis.

Thus this invention provides a method for inhibiting the symptoms induced by SRS-A in a mammal susceptible to said SRS-A which comprises administering to said mammal an amount effective for inhibiting said symptoms of a compound selected from the group consisting of 9-benzoyl-1,2,3,4-tetrahydrocarbazole-3-carboxylic acid, 9-benzoyl-6-methoxy-1,2,3,4-tetrahydrocarbazole-3-carboxylic acid, 9-benzoyl-1,2,3,4-tetrahydrocarbazole-4-carboxylic acid, 9-(4-toluoyl)-1,2,3,4-tetrahydrocarbazole-4-carboxylic acid, 9-benzoyl-6-methoxy-1,2,3,4-tetrahydrocarbazole-4-carboxylic acid and 9-benzoyl-6-methyl-1,2,3,4-tetrahydrocarbazole-4-carboxylic acid; or a pharmaceutically acceptable salt of said compound.

DETAILED DESCRIPTION INCLUSIVE OF THE PREFERRED EMBODIMENTS

In a preferred method of the invention, 9-benzoyl-6-methoxy-1,2,3,4-tetrahydrocarbazol-3-carboxylic acid or a pharmaceutically acceptable salt thereof is administered.

The compounds employed in the method of this invention are known compounds which are described, together with the methods for their preparation, in U.S. Pat. No. 3,948,939. Thus general methods for the preparation of the class of compounds which embraces the compounds employed in the method of this invention, as well as the methods of preparation of each of the compounds employed in the method of this invention are disclosed in U.S. Pat. No. 3,948,939 in columns 6 to 15 and in Examples 1, 21, 34, 35, 36 and 39, which disclosure is incorporated herein by reference. However, U.S. Pat. No. 3,948,939 neither discloses or suggests that the compounds employed in the method of this invention are antagonists of SRS-A and hence useful for the prophylactic treatment of symptoms induced by SRS-A.

The compounds employed in the method of this invention can be represented, in free acid form, by the structural formula

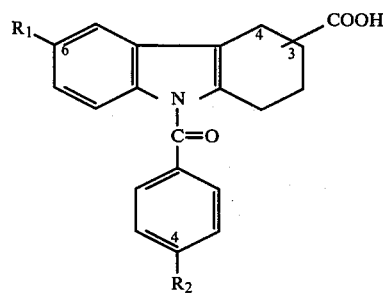

Thus, with reference to the above structural formula, the compounds named hereinabove respectively are those where $R_1$, $R_2$ and the position of COOH are as tabulated in Table 1 below. Table 1 identifies, in the last column thereof, the number of the Example in U.S. Pat. No. 3,948,939 describing the preparation of the indicated compound.

TABLE I

| Compound | $R_1$ | $R_2$ | Position of COOH | Example No. in USP 3,948,939 |
|---|---|---|---|---|
| a | H | H | 3 | 1 |
| b | OCH₃ | H | 3 | 21 |

TABLE I-continued

| Compound | $R_1$ | $R_2$ | Position of COOH | Example No. in USP 3,948,939 |
|---|---|---|---|---|
| c | H | H | 4 | 34 |
| d | H | $CH_3$ | 4 | 35 |
| e | $OCH_3$ | H | 4 | 36 |
| f | $CH_3$ | H | 4 | 39 |

The compounds employed in the method of this invention, by virtue of possessing a carboxylic acid group, are convertible to the corresponding pharmaceutically acceptable salt form using standard procedures, e.g., by interaction of a particular acid with a base, and such pharmaceutically acceptable salts are considered to be the full equivalents of the free acids in practicing the method of this invention. Examples of such pharmaceutically acceptable salts are those derived from heavy metals such as zinc and iron (ferrous, ferric); alkali metal salts such as sodium, potassium and lithium; alkali earth metal salts such as calcium and barium; aluminum and magnesium salts; and ammonium salts such as those derived from ammonia or amines, for example, methylamine, ethylamine, isopropylamine, dimethylamine, diethylamine, trimethylamine, dihexylamine, pyrrolidine, piperidine, choline, glucosamine, methylglucamine, 2-hydroxyethylamine, bis(2-hydroxyethylamine), tris(2-hydroxyethylamine), lysine, arginine and the like. Interaction of the acid and base is carried out in aqueous solution which can include, if desirable, an inert water-miscile organic solvent such as methyl alcohol or ethyl alcohol, at room or elevated temperature. When divalent or trivalent metal salts are prepared, approximately one-half molar or one-third molar equivalent respectively of the base are employed.

The following example describes the preparation of the sodium salt of 9-benzoyl-6-methoxy-1,2,3,4-tetrahydrocarbazole-3-carboxylic acid:

9-Benzoyl-6-methoxy-1,2,3,4-tetrahydrocarbazole-3-carboxylic acid (90 g) was added to a solution of sodium bicarbonate (28 g) in water (550 ml) to which methyl alcohol (60 ml) had been added. The resulting mixture was stirred and heated on a steam bath until a clear solution resulted and evolution of carbon dioxide ceased (30 minutes). The solution was slowly cooled to 5° C. and the resulting solid was separated, washed two times with ice water (20 ml each time) and two times with ether (100 ml each time) and dried at 25° C. for twelve hours and at 60° C. in vacuo for four hours. The yield of sodium 9-benzoyl-6-methoxy-1,2,3,4-tetrahydrocarbazole-3-carboxylate was 78 g.

The SRS-A antagonist activity of the compounds employed in the method of the invention was assessed in the following in vivo test procedure:

Test Procedure 1—Antagonism of SRS-A-Induced Bronchoconstriction In Unanesthetized Guinea Pigs SRS-A was prepared using a slightly modified procedure of Stechschulte et al. [J. Exp. Med., 125: 127, (1967)]. In this procedure, SRS-A is harvested from rat peritoneal cavity following an antigen/antibody reaction in the presence of polymorphonuclear leucocytes. Rabbit antiserum against bovine serum albumin (BSA) was used as the antibody. The peritoneal fluid containing SRS-A was analyzed for its potency before each experiment and a standardized amount of SRS-A ($ALD_{50}$-75) was injected intravenously into guinea pigs previously medicated (30 minutes, subcutaneously) with 10 mg/kg propranolol and 2 mg/kg diphenhydramine. The test compounds were administered orally to four guinea pigs/group 1 hour before the SRS-A challenge. The test compounds were prepared as suspensions in 1% gum tragacanth. Bronchoconstriction was graded 1+ to 3+ according to severity (1+ denoted restlessness and slight thoracic dyspnea, 2+ denoted moderate thoracic dyspnea and 3+ denoted convulsive dyspnea, regardless of whether the guinea pig died of asphyxiation or recovered). The test compounds were evaluated for their dose-related response in one or several multiple dose tests and their $AED_{50}$ values and potencies in terms of phenylbutazone as anti-SRS-A reference standard were calculated. The results are tabulated in Table II below.

TABLE II

| Compound | Potency (Phenylbutazone = 1) (95% confidence limits) | No. of Experiments | $AED_{50}$ mg/kg, p.o. |
|---|---|---|---|
| a | 1.1 (0.5-3.8) | 1 | 10 |
| b | 4.0 (2.1-8.2) | 3 | 2.3 |
| c | 16 (6.9-37) | 2 | 0.3 |
| d | 1.7 (0.6-6.8) | 2 | 5.0 |
| e | 18 (5.0-86) | 1 | 1.0 |
| f | 6.7 (3.2-16) | 2 | 1.7 |

The efficacy in terms of incidence of severe (3+) bronchospasm of compound b (9-benzoyl-6-methoxy-1,2,3,4-tetrahydrocarbazole-3-carboxylic acid) and, for purposes of comparison, phenylbutazone was examined at multiple doses in the above described test procedure. The results are tabulated in Table III below.

TABLE III

| Compound | Dose (mg/kg) p.o. | Incidence of Severe Bronchospasms | |
|---|---|---|---|
| | | No. Bronchosp./ No. Tested | % |
| b | 400 | 0/10 | 0 |
| | 100 | 0/20 | 0 |
| | 25 | 1/23 | 4 |
| | 6.2 | 0/19 | 0 |
| | 1.6 | 8/19 | 42 |
| | 0.4 | 15/20 | 75 |
| Phenylbutazone | 100 | 2/46 | 4 |
| | 25 | 21/147 | 15 |
| | 6.2 | 29/86 | 34 |
| | 1.6 | 47/77 | 62 |
| Pooled Controls | — | 328/368 | 89 |

As shown in Table III, an oral dose of 6.2 mg/kg of compound b completely inhibited severe SRS-A induced bronchospasm in guinea pigs.

Antagonism of SRS-A induced bronchoconstriction by compound b was also studied in anesthetized guinea pigs and compared to phenylbutazone in the following test procedure:

Test Procedure 2

SRS-A was harvested as described in Test Procedure 1 described hereinabove. A slightly modified Konzett-Rössler preparation [Arch. Exp. Pharm., 195: 71, (1940)] was used to measure increases in resistance to artificial lung inflation. Guinea pigs weighing 350 to 450 g were anesthetized ip with 1.5 g/kg urethane. The jugular vein and trachea were cannulated and the guinea pigs were artificially respired at a rate of 40 strokes/minute. Tidal volume was adjusted as a function of body weight, according to Kleinman and Radford (Harvard Physiological Apparatus Co., Bulletin No. 607, August 1966). A side arm of the inflationary air cannula was connected to a pressure transducer and resistance to pulmonary inflation continuously recorded. Bronchoconstrictor responses were suppressed in most of the guinea pigs if challenged immediately following the start of artificial respiration, hence, the bronchoconstrictor responsiveness was monitored by repeated iv injections of 5 mcg histamine/kg. Studies with SRS-A commenced after each guinea pig had attained maximum bronchoconstrictor response to histamine. Repeated injections of SRS-A resulted in tachyphylaxis, hence, SRS-A was injected into each guinea pig only once. The effects of the test compounds were studied by measuring SRS-A-induced bronchoconstriction side-by-side in two guinea pigs, one medicated and one control. Subsequent medicated/control pairs were alternated on two respiratory pumps. In this manner, the gradual decomposition of SRS-A and differences between the two pump/recorder systems, if any, were controlled. The dose (volume) of each sample of SRS-A was adjusted in each pair to keep the peaks of increases in bronchial resistance in control guinea pigs within 13 to 40 mmHg. Bronchoconstriction following injection of SRS-A was measured two ways; as the peak increase in resistance to inflation and, in view of the occasional irregular bronchoconstriction response curves following injection of SRS-A, as the sum of increases in bronchoconstriction over 10 minutes (pressure/time units). Pressure/time units were calculated by measuring the area under the curve of inflationary resistance where ordinates were set at 10 mm of pen excursion/10 mm pressure Hg and the abscissas were set at 15 mm of paper travel/minute. A typical normal base line resistance to inflation of 10 mm Hg over 10 minutes would be read as 212 pressure/time units. SRS-A-induced bronchoconstriction (increase in resistance) was calculated as the area under the curve and over the normal base line of resistance to inflation. Thus, the 274 pressure/time units for the procedure controls in Table V below represent the SRS-A-induced increase in resistance to inflation. Approximately 212 units would have to be added for the total pressure/time units over 10 minutes. The 10-minute interval was chosen because all peaks of resistance occurred within this time interval.

The effects of the test compounds upon SRS-A-induced bronchoconstriction were expressed as ratios of the peaks and as ratios of the pressure/time units between the paired medicated and control guinea pigs. The consistency of paired responses to SRS-A in nonmedicated guinea pigs was determined in the same manner, by alternating the ratios of the results of guinea pigs on pumps one and two. Compound b and phenylbutazone were administered intravenously, immediately followed by intravenous injections of 100 mcg/kg of propranolol and thenyldiamine. SRS-A was injected 5 minutes after these latter injections. Compound b was prepared as a solution in 2% N-methylglucamine and used within 3 hours. Phenylbutazone was prepared as a solution in 0.05 N NaOH. Both test compounds were administered in a volume of 1 ml/kg except for the 33 mg/kg dose of phenylbutazone and its control which were administered at 3.3 ml/kg. Control guinea pigs received injections of the respective solvent vehicles. In order to compare the activities of compound b following iv and po routes of administration, compound b was also administered orally. Guinea pigs were fasted 18 hours before the experiment, and compound b was administered as a fresh solution in 2% N-methylglucamine in a volume of 1 ml/100 g body weight. Control guinea pigs received 2% N-methylglucamine. Fifteen minutes later, the guinea pigs were anesthetized, cannulated, and prepared for injections of SRS-A as described. The procedure was timed so that SRS-A was injected 1 hour after the oral administration of compound b. In a separate experiment, using the same methodology, the duration anti-SRS-A activity of compound b was determined after oral administration. Compound b was finely ground in a tissue homogenizer and prepared as a suspension in 0.5% gum tragacanth. A dose of 10 mg/kg was administered and anti-SRS-A effect studied at 1, 4 and 7 hr postmedication. The ratios of peak increases in intratracheal pressure between paired medicated and control guinea pigs was used to calculate percent inhibition.

The results obtained in Test Procedure 2 are tabulated in Tables IV, V and VI below.

TABLE IV

INHIBITION OF SRS-A-INDUCED BRONCHOCONSTRICTION
(PEAKS OF INCREASES IN RESISTANCE TO PULMONARY INFLATION)

| Compound | Route | Dose (mg/kg) | No. Guinea Pig Pairs | Avg Controls* mmHg ± S.E. | Avg Ratio of Med/Co. Pairs | % Inhibition |
|---|---|---|---|---|---|---|
| (Controls: no test compound) | SRS-A iv, | | 8 | 27 ± 3 | 0.97 ± .06 | — |
| Compound b | i.v. | 10 | 5 | 29 ± 4 | 0.05 ± .03 | 95 |
| | | 3.3 | 6 | 29 ± 3 | 0.11 ± .04 | 89 |
| | | 1.0 | 6 | 27 ± 3 | 0.44 ± .07 | 54 |
| | | 0.33 | 8 | 23 ± 2 | 1.10 ± .19 | 0 |
| Phenylbutazone | i.v. | 33 | 5 | 39 ± 3 | 0.11 ± .04 | 89 |
| | | 10 | 7 | 22 ± 3 | 0.28 ± .08 | 72 |
| | | 3.3 | 6 | 23 ± 3 | 0.41 ± .13 | 59 |
| | | 1.0 | 8 | 22 ± 2 | 1.10 ± .19 | 0 |
| Compound b | p.o. | 10 | 5 | 28 ± 4 | 0.13 ± .04 | 87 |
| | | 3.3 | 5 | 23 ± 2 | 0.64 ± .13 | 36 |

*Vehicle of the respective medication.

TABLE V

INHIBITION OF SRS-A-INDUCED BRONCHOCONSTRICTION
(SUMS OF INCREASES IN RESISTANCE TO PULMONARY INFLATION)

| Compound | Route | Dose (mg/kg) | No. Guinea Pig Pairs | Avg Controls** P/T* Units ± S.E. | Avg Ratio Med/Co. Pairs | % Inhibition |
|---|---|---|---|---|---|---|
| (Controls: SRS-A iv, no test compound) | | | 8 | 274 ± 48 | 0.93 ± .16 | — |
| Compound b | i.v. | 10 | 5 | 343 ± 93 | 0.14 ± .04 | 86 |
| | | 3.3 | 6 | 302 ± 22 | 0.17 ± .05 | 83 |
| | | 1.0 | 6 | 298 ± 17 | 0.55 ± .09 | 45 |
| | | 0.3 | 8 | 280 ± 38 | 1.18 ± .33 | 0 |
| Phenyl-butazone | i.v. | 33 | 5 | 402 ± 64 | 0.10 ± .03 | 90 |
| | | 10 | 7 | 289 ± 34 | 0.19 ± .04 | 81 |
| | | 3.3 | 6 | 258 ± 41 | 0.44 ± .37 | 56 |
| | | 1.0 | 8 | 289 ± 48 | 1.33 ± .33 | 0 |
| Compound b | p.o. | 10 | 5 | 378 ± 37 | 0.08 ± .03 | 92 |
| | | 3.3 | 5 | 386 ± 30 | 0.53 ± .13 | 47 |

*Pressure/time (mmHg/10 min) units
**Vehicle of the respective medication

TABLE VI

Duration Of Anti-SRS-A Effect Of Compound b In Guinea Pigs

| Compound b Dosage mg/kg p.o. | Hr. Before Test | No. Guinea Pig Pairs | Ratio of Peak Response to SRS-A in Paired Med./Co. Guinea Pigs ± S.E. | % Inhibition | P |
|---|---|---|---|---|---|
| 10 | 1 | 6 | 0.19 ± 0.05 | 81 | 0.01 |
| | 4 | 6 | 0.32 ± 0.08 | 68 | 0.01 |
| | 7 | 11 | 1.00 ± 0.15 | 0 | — |

As shown in Tables IV and V, intravenously administered compound b or phenylbutazone inhibited SRS-A-induced increases in resistance to inflation in a dose-related manner. The minimal active dose for compound b was 1.0 mg/kg, and nearly complete inhibition was attained with 10 and 33 mg/kg of phenylbutazone.

The potency of compound b was calculated by the peaks of increases in resistance, since this parameter was more consistent than increases in pressure/time units. Compound b was 3.8 (95% confidence limits of 1.8 to 7.8) times more potent than phenylbutazone.

Orally administered solutions of compound b also resulted in dose-related inhibition (Tables IV and V). A dose of 10 mg/kg provided a nearly complete inhibition of SRS-A-induced bronchoconstriction. The iv/po activity ratio in terms of po AED50/iv AED50 was 2.6. This relatively low activity ratio suggests that compound b as a solution in 2% N-methylglucamine is readily absorbed from the GI tract.

In the separate duration experiment (Table VI), compound b inhibited SRS-A-induced bronchoconstriction for 4 hours following a single oral dose of 10 mg/kg administered as a suspension.

The effect of compound b against SRS-A-induced bronchoconstriction was studied in anesthetized cats and compared to phenylbutazone in the following test procedure.

Test Procedure 3

Mongrel cats, weighing 2.0 to 4.5 kg were anesthetized ip with 45 mg/kg of sodium pentobarbital. The trachea of each cat was cannulated, and the cats were artificially respired at 15 strokes/minute with a stroke volume of 22 ml/kg. A side-arm of the intratracheal cannula was connected to a Statham transducer, and the intratracheal pressure was recorded continuously on a polygraph. One femoral vein was cannulated in all cats receiving intravenous administration of drugs. In addition, most of the cats were cannulated through the femoral artery; this cannula was attached to another Statham transducer, and the blood pressure of these cats recorded. All cats received 1.0 mg/kg of propranolol and 0.2 mg/kg of thenyldiamine intravenously 3 minutes before iv injection of SRS-A. SRS-A was obtained from rat peritoneal cavities as described previously in Test Procedure 1. Each pool of rat ip fluid containing SRS-A was dose-ranged and a dose selected that was estimated to cause an average increase in intrapulmonary resistance to inflation in control cats by 4-6 mmHg. Test dose volumes ranged from 1.0 to 2.0 ml/kg, iv. Each cat was observed for changes in resistance to inflation for 10 minutes after the SRS-A injection. Compound b was dissolved in 10% N-methylglucamine; phenylbutazone was dissolved in 0.05N sodium hydroxide. The desired iv dose of each test compound was diluted in saline in a volume of 0.1 ml/kg for compound b and 2.0 ml/kg for phenylbutazone. A group of control cats received 2.0 ml/kg phenylbutazone vehicle, 0.2N sodium hydroxide. Both test compounds and the sodium hydroxide vehicle were injected iv 5 minutes before the injections of SRS-A (2 minutes before the injection of propranolol and thenyldiamine). When the test compounds were administered orally, the cats were fasted overnight, and the solutions of test compounds were given via stomach tube to anesthetized cats 1 hour before the injection of SRS-A. The volumes were 2 ml/kg for compound b and 4 ml/kg for phenylbutazone.

The results obtained in Test Procedure 3 are tabulated in Table VII.

TABLE VII

SRS-A-Induced Increase In Resistance To Pulmonary Inflation In Anesthetized Cats

| Compound | Dose (mg/kg) | No. Cats | Max. Increase in Resistance to Pulm. Inflation mm Hg ± S.E. | % Inhibition |
|---|---|---|---|---|
| Oral | | | | |
| Compound b | 10.0 | 5 | 0.1 ± 0.1 | 98* |
| | 3.3 | 5 | 0.6 ± 0.5 | 85* |
| | 1.0 | 10 | 2.0 ± 0.8 | 49 |

TABLE VII-continued

SRS-A-Induced Increase In Resistance To Pulmonary Inflation In Anesthetized Cats

| Compound | Dose (mg/kg) | No. Cats | Max. Increase in Resistance to Pulm. Inflation mm Hg ± S.E. | % Inhibition |
|---|---|---|---|---|
| | 0.33 | 5 | 3.1 ± 0.3 | 25 |
| Controls | — | 12 | 4.1 ± 0.8 | — |
| Phenyl-butazone | 33.0 | 4 | 0.1 ± 0.1 | 98* |
| | 10.0 | 5 | 3.0 ± 0.9 | 25 |
| Controls Intravenous | — | 5 | 4.0 ± 1.2 | — |
| Compound b | 1.0 | 6 | 0.1 ± 0.1 | 98* |
| | 0.1 | 6 | 1.6 ± 0.5 | 73* |
| | 0.01 | 6 | 4.1 ± 1.3 | 30 |
| Phenyl-butazone | 33.0 | 7 | 0 | 100* |
| | 10.1 | 7 | 4.7 ± 1.5 | 21 |
| 0.2N NaOH | — | 5 | 5.2 ± 1.5 | 12 |
| Controls | — | 22 | 5.9 ± 0.6 | — |

*Significant at p ≤ 0.01

As shown in Table VII, compound b administered orally at 10.0 or 3.3 mg/kg resulted in nearly complete inhibition of SRS-A-induced increase in resistance to inflation, 98% and 85%, respectively. The oral ED50 of compound b was 1.0 0.5 mg/kg.

As shown in Table VII, compound b administered intravenously at 1.0 mg/kg produced complete inhibition of SRS-A-induced increase in resistance to inflation, except for a 0.5 mm Hg increase in one of seven cats. The iv ED50 of compound b was 28±24 mcg/kg. Phenylbutazone resulted in complete inhibition of SRS-A-induced increase in resistance to inflation at 33 mg/kg. The iv AED50 for phenylbutazone was 16 mg/kg. Control injections of 0.2N NaOH had no significant effect upon SRS-A-induced increase in resistance to inflation.

The competitive antagonism of SRS-A by compound b was studied in anesthetized guinea pigs in the following test procedure.

Test Procedure 4

The intratracheal pressure (ITP) of anesthetized, artificially respired guinea pigs (Konzett-Rössler preparation) was monitored and peak increases in ITP recorded. The basic methodology was the same as that described hereinabove for Test Procedure 2 except that the basic experimental unit was not two guinea pigs (medicated and control) but three guinea pigs examined in an uninterrupted sequence: a control guinea pig receiving the standard dose of SRS-A, a medicated guinea pig receiving the standard dose of SRS-A and a medicated guinea pig receiving a multiple dose of SRS-A. In this manner, the ratios of peak responses of the same sample of SRS-A could be determined for medicated/control guinea pigs (standard procedure), and for medicated guinea pigs receiving the standard dose of SRS-A. The multiple dose of SRS-A in these studies was either 3× or 6× the standard dose.

The results obtained in Test Procedure 4 are tabulated in Table VIII.

TABLE VIII

COMPETITIVE ANTAGONISM OF COMPOUND b TO SRS-A

| | | | | | | SRS-A-Induced Increase in Intra-Tracheal Pressure | |
|---|---|---|---|---|---|---|---|
| | | | | | | Ratio | Ratio |
| Compound b (mg/kg, iv) | SRS-A Lot | SRS-A Dose (ml/kg) Low | SRS-A Dose (ml/kg) High | No. of Exp. Units (3 g. pigs each) | mm Hg Controls Low Dose SRS-A | Low Dose SRS-A + Compound b Guinea Pig / Low Dose SRS-A Control Guinea Pig | High Dose SRS-A + Compound b Guinea Pig / Low Dose SRS-A Control Guinea Pig |
| 3.3 | A | 4 | 12 | 8 | 19 ± 2 | 0.12 ± 0.3 | 0.76 ± .20 |
| 2.0 | B | 2 | 12 | 5 | 13 ± 2 | 0.14 ± 0.7 | 2.14 ± .68 |

As shown in Table VIII, in the first series of experiments, an intravenous dose of 3.3 mg/kg of compound b resulted in a ratio of 0.12 between peak responses to SRS-A of medicated and control guinea pigs (88% inhibition). A three-fold increase in the dose of SRS-A for the medicated guinea pigs increased this ratio to 0.76 (24% inhibition). In the second series of experiments, 2.0 mg/kg of compound b and a different lot of SRS-A resulted in a ratio of 0.14 between the peak responses to SRS-A of medicated and control guinea pigs (86% inhibition). A six-fold increase in the dose of SRS-A for the medicated guinea pigs resulted in a ratio of 2.14 between the medicated and control guinea pigs (0% inhibition or an enhancement of SRS-A-induced increase in ITP). These data indicate that compound b inhibits SRS-A-induced bronchoconstriction in guinea pigs as a competitive antagonist to SRS-A.

The effect of compound b against histamine-induced bronchoconstriction was studied in anesthetized guinea pigs and compared to phenylbutazone and diphenhydramine in the following test procedure.

Test Procedure 5

Guinea pigs weighing 350 to 400 g were anesthetized ip with 1.5 g/kg urethane and prepared for measurements of resistance to pulmonary inflation using a slightly modified Konzett-Rössler method (see Test Procedure 2). Since most guinea pigs do not respond fully to histamine immediately after the start of artificial respiration, the bronchoconstrictor responsiveness was monitored by repeated iv injections of 5 mcg histamine (base)/kg. The experimental procedure was started after each guinea pig had attained its maximal, repeatable response to histamine. The guinea pigs were disconnected from the respiratory pump and compound b or phenylbutazone was administered sc. Artificial respiration was resumed 25 minutes later. Thirty minutes after the administration of one of the drugs, tne guinea pigs received two of three injections of histamine at 3-minute intervals. The average of these histamine responses (increases in resistance) was expressed as percent of the maximal histamine response obtained with the same guinea pig before the administration of the drug. In addition to sc administration, compound b was also studied following po administration. In these studies, the time interval between po medication and the secondary histamine challenges was increased to 45 minutes. Diphenhydramine was used as the reference compound for antihistaminic activity and phenylbutazone as the reference compound for SRS-A antagonism. Compound b was administered as a solution in 4% N-methylglucamine and phenylbutazone as a solution in 0.05 N NaOH.

The results obtained in Test Procedure 5 are tabulated in Table IX.

TABLE IX

Inhibition Of Histamineinduced Increase In Resistance To Pulmonary Inflation

| Compound | Vehicle | Route | Dose mg/kg | Volume mg/kg | No. Guinea Pigs | Histamine-Response in % of Premed. Histamine Response | % Inhibition |
|---|---|---|---|---|---|---|---|
| Compound b (sol.) | 4% MG* | sc | 100 | 5.0 | 5 | 92 ± 2 | 8 |
| — | 4% MG | sc | — | 5.0 | 5 | 90 ± 6 | 10 |
| Compound b (sol.) | 4% MG | po | 100 | 5.0 | 8 | 84 ± 26 | 16 |
| — | 4% MG | po | — | 5.0 | 5 | 90 ± 7 | 10 |
| Phenylbutazone | .05N NaOH | sc | 100 | 5.0 | 5 | 100 ± 6 | 0 |
| Diphenhydramine | water | sc | 1.00 | 1.0 | 5 | 24 ± 6 | 76 |
|  |  |  | 0.33 | 1.0 | 4 | 51 ± 17 | 49 |
|  |  |  | 0.10 | 1.0 | 5 | 94 ± 10 | 6 |
| — | saline | sc | — | 1.0 | 5 | 101 ± 3 | 0 |

*N-methylglucamine

As shown in Table IX, subcutaneous administration of compound b or phenylbutazone at 100 mg/kg, or oral administration of compound b at 100 mg/kg resulted in no significant inhibition of the histamine-induced bronchoconstriction. The validity of the antihistaminic assay was demonstrated by the dose-related inhibition of the histamine responses by diphenhydramine at doses up to 1.0 mg (base)/kg, administered subcutaneously.

Compound b was studied for its effect against serotonin-induced bronchoconstriction in anesthetized guinea pigs and compared to cyproheptadine in the following test procedure.

Test Procedure 6

Guinea pigs, weighing 275–340 g, were anesthetized and prepared for measurements of resistance to pulmonary inflation using a slightly modified Konzett-Rössler method (see Test Procedure 2). All guinea pigs received 0.1 mg/kg of propranolol iv and 5 minutes later, 50 mcg/kg of serotonin (creatinine complex) iv. Compound b or cyproheptadine were administered iv just before the injection of propranolol at 50 or 5 mg/kg, respectively. Compound b was prepared as a 5% solution in 5% N-methylglucamine and cyproheptadine as a 0.25% aqueous solution.

The results obtained in Test Procedure 6 are tabulated in Table X.

TABLE X

INHIBITION OF SEROTONIN-INDUCED INCREASE IN RESISTANCE TO PULMONARY INFLATION

| Group* | Dose (mg/kg, iv) | Increase in Resistance (mm Hg) | Inhibition % | P |
|---|---|---|---|---|
| Compound b | 50 | 45 ± 8 | 4 | insign. |
| Cyproheptadine | 5.0 | 5 ± 1 | 89 | 0.01 |
| Controls | — | 47 ± 7 | — | — |

*Five guinea pigs/group

As shown in Table X, injection of 50 mcg/kg of serotonin resulted in a severe but transient increase in resistance to pulmonary inflation in nonmedicated, control guinea pigs. Compound b had no inhibitory effect, whereas cyproheptadine, an antiserotonin agent, inhibited the increase in resistance to inflation by 89%.

The effect of compound b on acetylcholine-induced bronchoconstriction was studied and compared to aminophylline in the following test procedure.

Test Procedure 7

Guinea pigs, weighing 250–350 g were anesthetized with 1.5 g/kg i.p. of urethane and prepared for measurements of resistance to pulmonary inflation using a slightly modified Konzett-Rössler preparation (see Test Procedure 2). Histamine phosphate (5 μg/kg as base) was injected four times at 5 minute intervals in order to ascertain that the maximum bronchoconstrictor responsiveness has been obtained. Acetylcholine was injected intravenously at 15 g/kg 5 minutes following the last injection of histamine and the increase in intratracheal pressure was recorded. Compound b or aminophylline (100 mg/kg p.o.) or the control vehicle were administered to five guinea pigs each, 1 hour before the injection of acetylcholine (½ hour before the anesthesia).

The results obtained in Test Procedure 7 are tabulated in Table XI.

TABLE XI

Effects Of Compound b Against Acetylcholine-Induced Bronchoconstriction In Anesthetized Guinea Pigs

| Compound | mg/kg p.o. | N | Peak Increase in Intracheal Pressure mm Hg | % Inhibition |
|---|---|---|---|---|
| Compound b | 100 | 5 | 21 ± 4 | 9 |
| Aminophylline | 100 | 5 | 7 ± 1 | 70** |
| Controls | — | 6 | 23 ± 1 | 1 |

**Significant at $p \leq 0.01$

As shown in Table XI, compound b, at a dose of 100 mg/kg p.o., was inactive against acetylcholine-induced bronchoconstriction. The validity of Test Procedure 7 is demonstrated by the inhibition of acetylcholine responses by aminophylline at 100 mg/kg p.o.

The effect of compound b on bradykinin-induced bronchoconstriction was studies in anesthetized guinea pigs and compared to phenylbutazone in the following test procedure.

Test Procedure 8

Antagonism of bradykinin-induced bronchoconstriction in guinea pigs was determined by measuring increases in resistance to artificial pulmonary inflation (Konzett-Rössler preparation). Basic methodology is similar to that described previously in Test Procedure 2. Due to large variations in bronchoconstricting responses among individual guinea pigs, each guinea pig serves as its own control and was challenged with bradykinin twice. The second response to bradykinin was expressed as percent of the first response to bradykinin. There was a continuous decline in the responses to subsequent injections of bradykinin, but the response to the second injection of bradykinin in a sample of six guinea pigs was a rather predictable 81±5% of the first response. All guinea pigs having a first bradykinin response of less than 12 mm Hg were rejected as poor responders. Similarly, all guinea pigs were rejected whose inflationary pressure failed to return to normal level after the first injection of bradykinin; most of these animals were found to have inflammatory consolidation of the lungs. In order to augment the bronchoconstrictor response, each guinea pig received 100 mcg propranolol/kg, iv, 5 minutes before the first injection of bradykinin (30 mcg/kg, iv). The peak response to bradykinin was recorded, and after the resistance to inflation had returned to a normal level (9–12 mm Hg), the guinea pigs were injected with compound b or phenylbutazone. Five minutes after the injection of a test compound the guinea pigs received the second injection of bradykinin and the peak of the response determined. The effects of both test compounds were expressed as % inhibition of bradykinin-induced increase in bronchial resistance to forced inflation, as compared to the levels of bronchial resistance following iv administration of their respective solvent controls. Compound b was administered as a solution in 2% N-methylglucamine. phenylbutazone was administered as a Na salt solution in 0.05N NaOH. The doses of both test compounds ranged from 0.33 to 33 mg/kg. Each dose (and the solvent controls) were administered in a volume of 1 ml/kg, except for the 33 mg/kg dose, which was administered in a volume of 3.3 ml/kg.

The results obtained in Test Procedure 8 are tabulated in Table XII.

TABLE XII

Inhibition Of Bradykinin-Induced Increase In Resistance To Pulmonary Inflation

| Compound | Dose (mg/kg, iv) | Number Guinea Pigs | Average Increase In Bronchial Resistance (2nd Response in % of 1st Response ± S.E. | % Inhibition |
|---|---|---|---|---|
| None | — | 6 | 81 ± 5 | — |
| Compound b | 33.0 | 6 | 6 ± 4 | 93+ |
|  | 10.0 | 7 | 14 ± 5 | 84+ |
|  | 3.3 | 6 | 16 ± 3 | 81+ |
|  | 1.0 | 6 | 45 ± 7 | 48+ |
|  | 0.33 | 6 | 76 ± 13 | 12 |
| 2% N-methyl-gluc. control | — | 6 | 86 ± 6 | — |
| Na Phenyl-butazone | 33.0 | 7 | 40 ± 7* | 50+ |
|  | 10.0 | 8 | 35 ± 11 | 56+ |
|  | 3.3 | 6 | 40 ± 9 | 50+ |
|  | 1.0 | 6 | 64 ± 12 | 20 |
| 0.05 N NaOH control | — | 6 | 80 ± 5 | — |

*Avg 5 guinea pigs; phenylbutazone caused death of one guinea pig and irreversible increase in inflationary pressure in another.
+Significant ($p \leq 0.01$)

As shown in Table XII, compound b inhibited bradykinin-induced increases in bronchial resistance to inflation in a dose-related manner. The lowest dose of compound b that resulted in significant inhibition was 1.0 mg/kg iv. The three highest doses of compound b, 3.3, 10 and 33 mg/kg, resulted in nearly complete inhibition. No adverse effects were noted following any of the injections of compound b or its solvent, 2% N-methylglucamine. Phenylbutazone significantly inhibited bradykinin-induced increase in bronchial resistance at 3.3 and 10 mg/kg; maximal inhibition was 56% at 10 mg/kg. The highest dose, 33 mg/kg, resulted in death of one out of seven guinea pigs and irreversible increase in the bronchial resistance in another guinea pig. The remaining five guinea pigs had a further dose-related inhibition of bradykinin-induced bronchoconstriction. No adverse effects were noted following injections of 0.05N NaOH. Compound b was calculated to be 2.8 time more potent (95% confidence limits 1.1 to 8.8) than phenylbutazone as an inhibitor of bradykinin-induced bronchoconstriction in guinea pigs.

The activity profile of compound b, with respect to its effectiveness against SRS-A- or bradykinin-induced bronchoconstriction in guinea pigs and its ineffectiveness against histamine-, serotonin- and acetylcholine-induced bronchoconstriction in guinea pigs, is similar to that of other known antagonists of SRS-A such as aspirin, phenylbutazone and the fenamates, each of which also inhibit SRS-A- and bradykiin-induced bronchoconstrictin in guinea pigs but are ineffective against histamine-, serotinin- and acetylcholine-induced bronchoconstriction.

The oral toxicity of compound b at doses of 5.0, 32.0, 75.0 and 200 mg/kg/day for 5 weeks was studied in rhesus monkeys. At the dose levels of 5.0, 32.0 and 75.0 mg/kg, compound b was generally well tolerated. No gross or microscopic histophathologic changes were found and no mortality occurred. At the 200 mg/kg dose level, compound b was not well tolerated and two deaths attributed to medication occurred.

The oral toxicity of compound b at doses of 10.0, 40.0, 160, 640 mg/kg/day for 5 weeks was studies in Charles River CD albino rats. In terms of overt side-effects, compound b was well tolerated at all four dose levels, and no deaths attributable to medication occurred. At 640 mg/kg the mean values for the number of red blood cells, hemoglobin concentration and hematocrit were minimally lower than controls and the growth rate was slightly depressed in the male rat. At a dose level of 1280 mg/kg/day, compound b was not well tolerated and all rats died within 18 days.

Prophylactically effective amounts of compounds a-f or compositions containing prophylactically effective amounts of these compounds can be administered by methods well known in the art. Thus they can be administered, either singly or with other pharmaceutical agents, e.g., antagonists of mediators of anaphylaxis such as antihistamines, or anti-asthmatic steroids such as prednisone and prednisolone, orally, parenterally or by inhalation, e.g., in the form of an aerosol, micropulverized powder or nebulized solution. For oral administration they can be administered in the form of pills, tablets, capsules, e.g., in admixture with talc, starch, milk sugar or other inert ingredients, i.e, pharmaceutically acceptable carriers, or in the form of aqueous solutions, suspensions, encapsulated suspensions, gels, elixirs or aqueous alcoholic solutions, e.g., in admixture with sugar or other sweetening agents, flavorings, colorants, thickeners and other conventional pharmaceutical excipients. For parenteral administration, they can be administered in solutions or suspentions, e.g., as an aqueous or peanut oil solution or suspension using excipients and carriers conventional for this mode of administration. For administration as aerosols, they can be dissolved in a suitable pharmaceutically acceptable solvent, e.g., ethyl alcohol or water or combinations of miscible solvents, and mixed with a pharmaceutically acceptable propellant. Such aerosol compositions are packaged for use in a pressurized container fitted with an aerosol valve suitable for release of the pressurized composition. Preferrably the aerosol valve is a metered valve, i.e., one, which on activation, releases a predetermined effective dose of the aerosol composition.

In practicing the method of the invention, the dose of compounds a-f to be administered and the frequency of administration will be dependent on the potency and duration of activity of the particular compound to be administered and on the route of administration, as well as the severity of the condition, age of the mammal to be treated, etc. Doses of compounds a-f contemplated for use in practicing the method of the invention are about 0.01 to about 100 mg per kilogram of body weight per day, preferably about 0.1 to about 10 mg per kilogram of body weight per day, either as a single dose or in divided doses. The actual determination of the effective dose of a particular compound to be administered can be readily determined by those skilled in the art without the need for extensive experimentation. Prophylactic treatment of the mammal should be continued daily for prolonged periods of time.

I claim:

1. A method for inhibiting the symptoms induced by SRS-A in a mammal having an allergic condition in which SRS-A is a causative factor which comprises prophylactically administering to said mammal an amount effective for inhibiting said symptoms of a compound selected from the group consisting of 9-benzoyl-1,2,3,4-tetrahydrocarbazole-3-carboxylic acid, 9-benzoyl-6-methoxy-1,2,3,4-tetrahydrocarbazole-3-carboxylic acid, 9-benzoyl-1,2,3,4-tetrahydrocarbazole-4-carboxylic acid, 9-(4-toluoyl)-1,2,3,4-tetrahydrocarbazole-4carboxylic acid, 9-benzoyl-6-methoxy-1,2,3,4-tetrahydrocarbazole-4-carboxylic acid and 9-benzoyl-6-methyl-1,2,3,4-tetrahydrocarbazole-4-carboxylic acid; or a pharmaceutically acceptable salt of said compound.

2. The method according to claim 1 wherein the compound is administered orally.

3. The method according to claim 1 wherein the compound administered is 9-benzoyl-6-methoxy-1,2,3,4-tetrahydrocarbazole-3-carboxylic acid or a pharmaceutically acceptable salt thereof.

4. The method according to claim 3 wherein the compound is administered orally.

5. The method according to claim 3 wherein the compound administered is 9-benzoyl-6-methoxy-1,2,3,4-tetrahydrocarbazole-3-carboxylic acid.

6. The method according to claim 5 wherein the compound is administered orally.

7. A method for inhibiting the symptoms of allergic bronchial asthma induced by SRS-A in a mammal having said asthma which comprises prophylactically administering to said mammal an amount effective for inhibiting said symptoms of a compound selected from the group consisting of 9-benzoyl-1,2,3,4-tetrahydrocarbazole-3-carboxylic acid, 9-benzoyl-6-methoxy-1,2,3,4-tetrahydrocarbazole-3-carboxylic acid, 9-benzoyl-1,2,3,4-tetrahydrocarbazole-4-carboxylic acid, 9-(4-toluoyl)-1,2,3,4-tetrahydrocarbazole-4-carboxylic acid, 9-benzoyl-6-methoxy-1,2,3,4-tetrahydrocarbazole-4-carboxylic acid and 9-benzoyl-6-methyl-1,2,3,4-tetrahydrocarbazole-4-carboxylic acid; or a pharmaceutically acceptable salt of said compound.

8. The method according to claim 7 wherein the compound is administered orally.

9. The method according to claim 7 wherein the compound administered is 9-benzoyl-6-methoxy-1,2,3,4-tetrahydrocarbazole-3-carboxylic acid or a pharmaceutically acceptable salt thereof.

10. The method according to claim 9 wherein the compound is administered orally.

11. The method according to claim 9 wherein the compound administered is 9-benzoyl-6-methoxy-1,2,3,4-tetrahydrocarbazole-3-carboxylic acid.

12. The method according to claim 11 wherein the compound is administered orally.

* * * * *

UNITED STATES PATENT AND TRADEMARK OFFICE
CERTIFICATE OF CORRECTION

PATENT NO. : 4,174,402
DATED : November 13, 1979
INVENTOR(S) : Zigurd E. Mielens It is certified that error appears in the above-identified patent and that said Letters Patent are hereby corrected as shown below:

Column 10, Table VIII, "0.12 ± 0.3" should read -- 0.12 ± .03 -- and "0.14 ± 0.7" should read -- 0.14 ± .07 --.

Column 10, line 62, "tne" should read -- the --.

Column 13, Table XII, line 43, -- ) -- should be inserted after -- Response --.

Column 14, line 20, "bradykiin" should read -- bradykinin --.

Column 14, line 28, "histophathologic" should read -- histopathologic --.

Column 15, Claim 1, line 37, "-4carboxylic" should read -- -4-carboxylic --.

Signed and Sealed this

Eighth Day of April 1980

[SEAL]

Attest:

SIDNEY A. DIAMOND

Attesting Officer

Commissioner of Patents and Trademarks